United States Patent
Li et al.

(10) Patent No.: US 10,442,766 B1
(45) Date of Patent: Oct. 15, 2019

(54) METHOD AND PRODUCTION LINE FOR PREPARING 2,6-DICHLOROPYRIDINE THROUGH GAS PHASE PHOTOCHLORINATION OF PYRIDINE

(71) Applicant: Zhejiang Avilive Chemical Co., Ltd., Dongyang, Zhejiang (CN)

(72) Inventors: Huiyue Li, Zhejiang (CN); Keqiang Jin, Zhejiang (CN); Jiaquan Zhu, Zhejiang (CN)

(73) Assignee: Zhejiang Avilive Chemical Co., Ltd., Zhejiang (CN)

( * ) Notice: Subject to any disclaimer, the term of this patent is extended or adjusted under 35 U.S.C. 154(b) by 0 days.

(21) Appl. No.: 16/221,601

(22) Filed: Dec. 17, 2018

(30) Foreign Application Priority Data

Oct. 30, 2018 (CN) .......................... 2018 1 1272344

(51) Int. Cl.
| | |
|---|---|
| *C07D 213/61* | (2006.01) |
| *C07B 39/00* | (2006.01) |
| *B01D 3/14* | (2006.01) |
| *B01J 19/12* | (2006.01) |

(52) U.S. Cl.
CPC .......... *C07D 213/61* (2013.01); *B01D 3/143* (2013.01); *B01J 19/123* (2013.01); *C07B 39/00* (2013.01); *B01J 2219/00033* (2013.01); *B01J 2219/00051* (2013.01); *B01J 2219/0875* (2013.01)

(58) Field of Classification Search
CPC ................................................. C07D 213/61
USPC ....................................................... 546/345
See application file for complete search history.

(56) References Cited

U.S. PATENT DOCUMENTS 4,752,644 A * 6/1988 Sharvit ................ C07D 213/61
546/345

* cited by examiner

*Primary Examiner* — Taofiq A Solola
(74) *Attorney, Agent, or Firm* — Tony Hom, Esq.

(57) ABSTRACT

The present invention relates to a method for preparing 2,6-dichloropyridine with product purity greater than or equal to 99.0% through gas phase photochlorination of pyridine by using trifluoromethyl chlorobenzene as a solvent for reaction between pyridine and chlorine gas. Gasified pyridine and heated chlorine gas are enabled to continuously experience chlorination reaction under irradiation of ultraviolet light by using gasified pyridine and heated chlorine gas as starting materials and using heated trifluoromethyl chlorobenzene as a solvent, and a gas phase reaction product and the solvent are cooled to obtain pyridine chlorination solution. Advantages: firstly, it pioneers the precedent of direct and high-selectivity preparation of 2,6-dichloropyridine through gas phase photochlorination, and not only can the 2,6-dichloropyridine product with purity greater than or equal to 99.0% be obtained, but also industrial production is facilitated; and secondly, the selectivity of pyridine chlorination is high, the chlorination solution is subjected to crude distillation to separate high-boiling-point substances, the crude distillate is subjected to cooling crystallization or rectification to separate the solvent, the solvent is reused, and not only can the 2,6-dichloropyridine product with purity greater than or equal to 99.0% be obtained, but also the purposes of no pollution, low energy consumption and low cost can be realized.

10 Claims, No Drawings

METHOD AND PRODUCTION LINE FOR PREPARING 2,6-DICHLOROPYRIDINE THROUGH GAS PHASE PHOTOCHLORINATION OF PYRIDINE

TECHNICAL FIELD

The present invention relates to a method and production line for preparing 2,6-dichloropyridine with product purity greater than or equal to 99.0% by using trifluoromethyl chlorobenzene as a solvent for reaction between pyridine and chlorine gas.

BACKGROUND ART

At current, main synthetic methods of 2,6-dichloropyridine include: a gas phase photochlorination method of pyridine aqueous solution, in which an obtained main product is mixture of 2-chloropyridine and 2,6-dichloropyridine, the proportion of 2,6-dichloropyridine is generally 5%-50%, chloride materials need to be subjected to a series of steps, such as neutralization, crude distillation and rectification, to separate and purify 2,6-dichloropyridine, a great amount of wastewater and waste salt are produced, and the treatment cost of three wastes is high;

an ultraviolet-light-free direct-heating chlorination method of pyridine, in which the yield of 2,6-dichloropyridine is smaller than 30%, the coking rate is about 45%, a great amount of tar is produced and the treatment cost is high;

a liquid phase photochlorination method of 2-chloropyridine, in which the conversion rate of 2-chloropyridine is about 96% within 10 h and the yield of 2,6-dichloropyridine is about 93%, but there are some disadvantages such as blockage of tail gas pipeline by materials, the production process of the raw material 2-chloropyridine also causes the production of a great amount of wastewater and waste salt, and consequently the production cost is high.

SUMMARY OF THE INVENTION

Purpose of design: in order to avoid the shortcomings mentioned in the background art, a method and production line for preparing 2,6-dichloropyridine through gas phase photochlorination of pyridine, with the purity of the prepared 2,6-dichloropyridine product being greater than or equal to 99.0%, by using trifluoromethyl chlorobenzene as a diluent for reaction between pyridine and chlorine gas, are designed, which overcome the disadvantages such as that a great amount of three wastes are produced and the materials block the tail gas pipeline in the preparation methods mentioned in the background art, reduce the emission of three wastes, decrease the production cost, facilitate the industrial production, and realize low pollution, low energy consumption and low cost in preparation of the 2,6-dichloropyridine product with purity greater than or equal to 99.0%.

Use of design of the present invention: 2,6-dichloropyridine is an important chemical raw material, from which a variety of fine chemical products can be produced, and which is widely used in the fields of medicine, daily chemical industry, new insecticidal pesticides, etc. Secondly, 2,6-dichloropyridine is a main raw material for producing 2,3,5,6-tetrachloropyridine, sodium trichloropyridinol and 2,3-dichloropyridine, while sodium trichloropyridinol is a key intermediate for producing insecticide chlorpyrifos and weedicide chlorochlorpyridine, and 2,3-dichloropyridine is a key intermediate for producing new insecticide chlorantraniliprole.

In order to realize the purpose of design of the present invention, the present invention designs a method for preparing a 2,6-dichloropyridine product with purity greater than or equal to 99.0% through gas phase chlorination reaction at temperature of 150-250° C. under irradiation of ultraviolet light, by using pyridine and chlorine gas as starting materials, using trifluoromethyl chlorobenzene and the like as a diluent, and feeding heated chlorine gas, gasified pyridine and diluent, which is a main technical feature of the present invention. The purpose of such design is as follow: in industrial production, the ultraviolet light source is turned on, heated chlorine gas is firstly fed into the photochlorination reactor, then gasified pyridine and diluent are fed, heat is emitted during chlorination reaction, temperature rises, the reaction temperature is controlled in the range of 150-250° C. by adjusting the proportion of the diluent or the flow rate of coolant for cooling in the photochlorination reactor, and thus not only can the situations of low reaction temperature and slow reaction speed be avoided, but also the situations of high reaction temperature and easy coking and carbonization of materials can be avoided. In the process of gas phase photochlorination reaction, an ultraviolet light lamp in the chlorination reactor is turned on, heated chlorine gas is fed into the photochlorination reactor, at the same time gasified pyridine and trifluoromethyl chlorobenzene are mixed according to proportions, and then the mixture is added into the photochlorination reactor to continuously experience gas phase photochlorination reaction under irradiation of light. The gasified diluent can slow down the chlorination reaction, reduce the intensity of heat emission in reaction, avoid the material coking caused by excessive local temperature of reaction materials, and reduce the coking rate by 60%-70%. More importantly, not only can the yield be improved, but also the preparation efficiency of the 2,6-dichloropyridine product with purity greater than or equal to 99.0% is enabled to be more scientific and simple, the intermediate link in the background art is avoided, and unexpected technical effects are achieved, which are specifically reflected as follows:

Comparative test data of processes for preparing 2,6-dichloropyridine through gas phase photochlorination of pyridine

| Test comparison item | Preparation method | Coking rate | Yield of 2,6-dichloropyridine | Amount of produced wastewater and waste salt | Treatment cost of three wastes |
|---|---|---|---|---|---|
| Background art | Gas phase chlorination + liquid phase chlorination | 15% | 68.4% | 2.4 t (salt)/t | 2700 CNY/t |
| Background art | Liquid phase thermal chlorination | 45% | 50% | 1 t (tar)/t | 3000 CNY/t |
| Present invention | Gas phase chlorination | 13.05% | 79.23% | 1.6 t (HCl), 0.1 t (salt)/t | 370 CNY/t |

Technical solution: a method for preparing 2,6-dichloropyridine through gas phase photochlorination of pyridine, in which gasified pyridine and heated chlorine gas are enabled to continuously experience chlorination reaction at temperature of 150-250° C. under irradiation of ultraviolet light by using gasified pyridine and heated chlorine gas as starting materials and using gasified trifluoromethyl chlorobenzene as a diluent, and a gas phase reaction product and the solvent are cooled to obtain pyridine chlorination solution.

Compared with the background art, the present invention firstly pioneers the precedent of direct and high-selectivity preparation of 2,6-dichloropyridine through gas phase photochlorination, and not only can the 2,6-dichloropyridine product with purity greater than or equal to 99.0% be obtained, but also industrial production is facilitated; and secondly, the selectivity of pyridine chlorination is high, the chlorination solution is subjected to crude distillation to separate high-boiling-point substances, the crude distillate is subjected to cooling crystallization or rectification to separate the solvent, the solvent is reused, and not only can the 2,6-dichloropyridine product with purity greater than or equal to 99.0% be obtained, but also the purposes of no pollution, low energy consumption and low cost can be realized.

DESCRIPTION OF THE EMBODIMENTS

Embodiment 1: a method for preparing 2,6-dichloropyridine through gas phase photochlorination of pyridine, in which gasified pyridine and heated chlorine gas were enabled to continuously experience chlorination reaction at temperature of 150-250° C. under irradiation of ultraviolet light by using gasified pyridine and heated chlorine gas as starting materials and using gasified trifluoromethyl chlorobenzene as a diluent, and a gas phase reaction product and the diluent were cooled to obtain pyridine chlorination solution.

In this embodiment, gasified pyridine and trifluoromethyl chlorobenzene and heated chlorine gas simultaneously entered a photochlorination reactor to continuously experience chlorination reaction. The weight ratio of pyridine to the solvent to chlorine gas was 1:0.2-5:0.9-2. The amount of fed chlorine gas was 1.8-2.5 times the weight of pyridine. The ultraviolet light for irradiation came from an ultraviolet light source or blue light source with a wavelength of 254-400 nm. The solvent included, but not limited to, trifluoromethyl monochlorobenzene, trifluoromethyl dichlorobenzene and trifluoromethyl trichlorobenzene. In the chlorination reaction, heated chlorine gas was continuously fed, and at the same time the mixture of pyridine and solvent was continuously added according to proportions. The gas phase reaction product and the solvent were cooled to obtain pyridine chlorination solution.

Test data of conditions (chlorination materials) for preparing 2,6-dichloropyridine through gas phase photochlorination of pyridine

| Reaction temperature (° C.) | 150° C. | 175° C. | 195° C. | 205° C. | 250° C. |
|---|---|---|---|---|---|
| Weight of chlorination solution (g) | 2673.83 | 2813.21 | 2795.03 | 2755.64 | 2773.82 |
| Content of solvent (%) | 59.91 | 56.84 | 57.23 | 58.07 | 57.68 |
| Content of 2,6-dichloropyridine (%) | 26.82 | 25.49 | 25.66 | 26.03 | 25.86 |

Embodiment 2: on the basis of embodiment 1, gasified pyridine and heated chlorine gas were enabled to continuously experience chlorination reaction at temperature of 150-250° C. under irradiation of ultraviolet light by using gasified pyridine and heated chlorine gas as starting materials and using gasified trifluoromethyl chlorobenzene as a diluent, a gas phase reaction product and the solvent were cooled to obtain pyridine chlorination solution, the chlorination solution was subjected to crude distillation, then tar and high-boiling-point substances were separated, and the obtained distillate was pyridine chloride containing the solvent.

Test data of conditions (crude distillation materials) for preparing 2,6-dichloropyridine through gas phase photochlorination of pyridine

| Reaction temperature (° C.) | 150° C. | 175° C. | 195° C. | 205° C. | 250° C. |
|---|---|---|---|---|---|
| Weight of crude distillate (g) | 2460.01 | 2581.43 | 2567.26 | 2489.98 | 2463.27 |
| Content of solvent (%) | 61.87 | 58.85 | 59.19 | 61.06 | 61.71 |
| Content of 2,6-dichloropyridine (%) | 29.16 | 27.79 | 27.94 | 28.81 | 29.12 |
| Weight of tar (g) | 84.35 | 95.92 | 92.66 | 134.62 | 180.91 |
| Coking rate (%) | 11.88 | 13.51 | 13.05 | 18.96 | 25.48 |

Embodiment 3: on the basis of embodiment 1 and 2, gasified pyridine and heated chlorine gas were enabled to continuously experience chlorination reaction at temperature of 150-250° C. under irradiation of ultraviolet light by using gasified pyridine and heated chlorine gas as starting materials and using gasified trifluoromethyl chlorobenzene as a diluent, a gas phase reaction product and the solvent were cooled to obtain pyridine chlorination solution, the chlorination solution was subjected to crude distillation, then tar and high-boiling-point substances were separated, the obtained distillate was pyridine chloride containing the solvent, a 2,6-dichloropyridine product with purity greater than or equal to 99.0% was obtained through cooling crystallization separation, or the chlorination solution was subjected to crude distillation and then was purified by adopting a rectification method to obtain a 2,6-dichloropyridine product with purity greater than or equal to 99.0%, i.e., feeding was continuously performed to perform gas phase chlorination reaction at temperature of 150-250° C. under irradiation of ultraviolet light by using gasified pyridine and heated chlorine gas as starting materials and using gasified trifluoromethyl chlorobenzene as a solvent, a gas phase reaction product and the solvent were cooled to obtain pyridine chlorination solution, the chlorination solution was subjected to crude distillation, then tar and high-boiling-point substances were separated, the obtained distillate was pyridine chloride containing the solvent, the solvent was removed to obtain 2,6-dichloropyridine with purity greater than or equal to 99.0% from the pyridine chloride.

Test data of 2,6-dichloropyridine prepared through gas phase photochlorination of pyridine (crystallization separation)

| Reaction temperature (° C.) | 150° C. | 175° C. | 195° C. | 205° C. | 250° C. |
|---|---|---|---|---|---|
| Weight of product (g) | 691.21 | 1039.52 | 1000.86 | 680.00 | 572.56 |
| Content of product (%) | 99.56 | 99.23 | 99.42 | 99.55 | 99.21 |
| Yield of product (%) | 51.81 | 77.65 | 74.91 | 50.96 | 42.76 |

Embodiment 4: on the basis of embodiment 1 and embodiment 2, feeding was continuously performed to perform gas phase chlorination reaction at temperature of 150-250° C. under irradiation of ultraviolet light by using gasified pyridine and heated chlorine gas as starting materials and using gasified trifluoromethyl chlorobenzene as a solvent, a gas phase reaction product and the solvent were cooled to obtain pyridine chlorination solution, the chlorination solution was subjected to crude distillation and then was purified by adopting a rectification method to obtain a 2,6-dichloropyridine product with purity greater than or equal to 99.0%.

Test data of 2,6-dichloropyridine prepared through gas phase photochlorination of pyridine (rectification separation)

| Reaction temperature (° C.) | 150° C. | 175° C. | 195° C. | 205° C. | 250° C. |
|---|---|---|---|---|---|
| Weight of product (g) | 705.31 | 1060.73 | 1021.28 | 693.87 | 584.24 |
| Content of product (%) | 98.01 | 99.22 | 99.15 | 99.07 | 99.04 |
| Yield of product (%) | 52.04 | 79.23 | 76.23 | 51.75 | 43.56 |

The rectification purification method was to separate and purify 2,6-dichloropyridine from pyridine chloride containing the solvent to obtain the product with purity greater than or equal to 99.0% and the solvent with purity greater than or equal to 95.0%, wherein the solvent was reused.

Description will be made through examples:

Example 1

1. An ultraviolet lamp was turned on, chlorine gas was fed after temperature of a gas phase photochlorination reactor was increased to 140° C., and the flow rate was 490 ml/min.
2. Temperature of a solvent gasifier was increased to 220° C., trifluoromethyl trichlorobenzene was dripped, and the dripping speed was controlled to be 1 ml/min.
3. Temperature of a pyridine gasifier was increased to 120° C., pyridine was dripped, the dripping speed was controlled to be 0.7 ml/min, the temperature was increased gradually with reaction, and finally the reaction temperature was controlled to be 150-250° C.
4. Gas discharged from an outlet of the reactor was cooled by a condenser, and the condensed chlorination reaction solution flowed into a 3000 ml collection bottle. Feeding was continuously performed for chlorination reaction until 710 g of pyridine and 1656 g of trifluoromethyl trichlorobenzene were completely dripped.
5. After reaction was completed, the taken-out condensed chlorination reaction solution was washed and stratified with water, and the oil layer was subjected to reduced pressure distillation until no distillate was evaporated obviously. The residual solution was tar and weighed.
6. The evaporated distillate was heated and melted, then temperature was slowly decreased to below 20° C. under stirring, then stirring at heat preservation was continuously performed for 1 h below 20° C. until the product was fully precipitated, and then filtration was performed.

Filter cake rectification was performed to remove the solvent to obtain the 2,6-dichloropyridine product with purity greater than or equal to 99.0%. Filtrate rectification was performed to recover the product and the diluent, and the diluent was directly applied.

Test data of 2,6-dichloropyridine prepared through gas phase photochlorination of pyridine (different temperature)

| Reaction temperature (° C.) | 150° C. | 175° C. | 195° C. | 205° C. | 250° C. |
|---|---|---|---|---|---|
| Weight of product (g) | 691.21 | 1039.52 | 1000.86 | 680.00 | 572.56 |
| Content of product (%) | 99.56 | 99.23 | 99.42 | 99.55 | 99.21 |
| Coking rate (%) | 11.88 | 13.51 | 13.05 | 18.96 | 25.48 |
| Yield of product (%) | 51.81 | 77.65 | 74.91 | 50.96 | 42.76 |

Example 2

1. An ultraviolet lamp was turned on, chlorine gas was fed after temperature of a gas phase photochlorination reactor was increased to 140° C., and the flow rate was 390-590 ml/min.
2. Temperature of a solvent gasifier was increased to 220° C., trifluoromethyl trichlorobenzene was dripped, and the dripping speed was controlled to be 1 ml/min.
3. Temperature of a pyridine gasifier was increased to 120° C., pyridine was dripped, the dripping speed was controlled to be 0.7 ml/min, the temperature was increased gradually with reaction, and finally the reaction temperature was controlled to be 175° C.
4. Gas discharged from an outlet of the reactor was cooled by a condenser, and the condensed chlorination reaction solution flowed into a 3000 ml collection bottle. Feeding was continuously performed for chlorination reaction until 710 g of pyridine and 1656 g of trifluoromethyl trichlorobenzene were completely dripped.
5. After reaction was completed, the taken-out condensed chlorination reaction solution was washed and stratified with water, and the oil layer was subjected to reduced pressure distillation until no distillate was evaporated obviously. The residual solution was tar and weighed.
6. Rectification was performed to crude distillate to remove the solvent and other components to obtain the 2,6-dichloropyridine product with purity greater than or equal to 99.0%.

Test data of 2,6-dichloropyridine prepared through gas phase photochlorination of pyridine (different chlorine gas amounts)

| Chlorine gas speed (ml/min) | 390 | 440 | 490 | 540 | 590 |
|---|---|---|---|---|---|
| Weight of product (g) | 745.49 | 949.94 | 1060.73 | 1031.65 | 1032.57 |
| Content of product (%) | 99.00 | 99.06 | 99.22 | 99.12 | 99.07 |
| Coking rate (%) | 20.31 | 14.65 | 13.51 | 11.33 | 11.02 |
| Yield of product (%) | 55.56 | 70.84 | 79.23 | 76.98 | 77.01 |

Example 3

1. An ultraviolet lamp was turned on, chlorine gas was fed after temperature of a gas phase photochlorination reactor was increased to 140° C., and the flow rate was 490 ml/min.
2. Temperature of a solvent gasifier was increased to 220° C., trifluoromethyl trichlorobenzene was dripped, and the dripping speed was controlled to be 0.04-3.9 ml/min.
3. Temperature of a pyridine gasifier was increased to 120° C., pyridine was dripped, the dripping speed was controlled to be 0.7 ml/min, the temperature was increased gradually with reaction, and the reaction temperature was controlled to be 175° C.
4. Gas discharged from an outlet of the reactor was cooled by a condenser, and the condensed chlorination reaction solution flowed into a 3000 ml collection bottle. Feeding was continuously performed for chlorination reaction until 710 g of pyridine and 126-2760 g of trifluoromethyl trichlorobenzene were completely dripped.

Other steps are the same as those in example 2.

Test data of 2,6-dichloropyridine prepared through gas phase photochlorination of pyridine (different ratios of pyridine to diluent)

| Pyridine:diluent (W:W) | 1:4 | 1:2.3 | 1:1 | 1:0.54 | 1:0.18 |
|---|---|---|---|---|---|
| Weight of product (g) | 1090.46 | 1060.73 | 1007.53 | 963.52 | 875.43 |

-continued

Test data of 2,6-dichloropyridine prepared through gas phase photochlorination of pyridine (different ratios of pyridine to diluent)

| Content of product (%) | 99.11 | 99.22 | 99.04 | 99.07 | 99.13 |
|---|---|---|---|---|---|
| Coking rate (%) | 8.96 | 13.51 | 15.14 | 20.46 | 28.84 |
| Yield of product (%) | 81.36 | 79.23 | 75.12 | 71.86 | 65.33 |

It needs to be understood that, although the above-mentioned embodiments give more detailed descriptions of the design concept of the present invention, these descriptions are only simple descriptions of the design concept of the present invention, instead of limitations to the design concept of the present invention, and any combination, addition or modification that does not go beyond the design concept of the present invention shall fall within the protection scope of the present invention.

What is claimed is:

1. A method for preparing 2,6-dichloropyridine through gas phase photochlorination of pyridine, wherein gasified pyridine and heated chlorine gas are enabled to continuously experience chlorination reaction at temperature of 150-250° C. under irradiation of ultraviolet light by using gasified pyridine and heated chlorine gas as starting materials and using heated trifluoromethyl chlorobenzene as a solvent, and a gas phase reaction product and the solvent are cooled to obtain pyridine chlorination solution.

2. The method for preparing 2,6-dichloropyridine through gas phase photochlorination of pyridine according to claim 1, wherein gasified pyridine and heated chlorine gas are enabled to continuously experience chlorination reaction at temperature of 150-250° C. under irradiation of ultraviolet light by using gasified pyridine and heated chlorine gas as starting materials and using heated trifluoromethyl chlorobenzene as a solvent, a gas phase reaction product and the solvent are cooled to obtain pyridine chlorination solution, the chlorination solution is subjected to crude distillation, then tar and high-boiling-point substances are separated, the obtained distillate is pyridine chloride containing the solvent, and the content of 2,6-dichloropyridine in the pyridine chloride after the solvent is removed is greater than or equal to 65%.

3. The method for preparing 2,6-dichloropyridine through gas phase photochlorination of pyridine according to claim 1, wherein gasified pyridine and heated chlorine gas are enabled to continuously experience chlorination reaction at temperature of 150-250° C. under irradiation of ultraviolet light by using gasified pyridine and heated chlorine gas as starting materials and using heated trifluoromethyl chlorobenzene as a solvent, a gas phase reaction product and the solvent are cooled to obtain pyridine chlorination solution, the chlorination solution is subjected to crude distillation, then tar and high-boiling-point substances are separated, the obtained distillate is pyridine chloride containing the solvent, a 2,6-dichloropyridine product with purity greater than or equal to 99.0% is obtained through cooling crystallization after the chlorination solution is subjected to crude distillation to separate tar and high-boiling-point substances, or the chlorination solution is subjected to crude distillation and then is purified by adopting a rectification method to obtain a 2,6-dichloropyridine product with purity greater than or equal to 99.0%.

4. The method for preparing 2,6-dichloropyridine through gas phase photochlorination of pyridine according to claim 1, wherein gasified pyridine, heated trifluoromethyl chlorobenzene and heated chlorine gas are simultaneously and continuously fed into a photochlorination reactor for continuous chlorination reaction.

5. The method for preparing 2,6-dichloropyridine through gas phase photochlorination of pyridine according to claim 1, wherein the weight ratio of pyridine to the solvent to chlorine gas is 1:0.1-9:1.8-2.7.

6. The method for preparing 2,6-dichloropyridine through gas phase photochlorination of pyridine according to claim 1, wherein the rectification purification method is to separate and purify 2,6-dichloropyridine from the crude product containing the solvent to obtain the product with purity greater than or equal to 99.0% and the solvent with purity greater than or equal to 95.0%, wherein the solvent is reused.

7. The method for preparing 2,6-dichloropyridine through gas phase photochlorination of pyridine according to claim 3, wherein the crystallization separation purification method is to separate and purify 2,6-dichloropyridine from the crude product containing the solvent through cooling crystallization to obtain the product with purity greater than or equal to 99.0% and the solvent with purity greater than or equal to 95.0%, wherein the solvent is reused; and the solvent and part of the product are recovered from the crystallization mother solution through a rectification method.

8. The method for preparing 2,6-dichloropyridine through gas phase photochlorination of pyridine according to claim 1, wherein the ultraviolet light for irradiation comes from an ultraviolet light source or blue light source with a wavelength of 254-400 nm.

9. The method for preparing 2,6-dichloropyridine through gas phase photochlorination of pyridine according to claim 1, wherein the solvent includes, but not limited to, trifluoromethyl monochlorobenzene, trifluoromethyl dichlorobenzene and trifluoromethyl trichlorobenzene.

10. The method for preparing 2,6-dichloropyridine through gas phase photochlorination of pyridine according to claim 1, wherein, when the chlorination reaction temperature exceeds a normal range, the trifluoromethyl chlorobenzene solvent is sprayed into the chlorination reactor to control the reaction temperature.

* * * * *